US007001071B2

(12) United States Patent
Deuringer et al.

(10) Patent No.: US 7,001,071 B2
(45) Date of Patent: Feb. 21, 2006

(54) METHOD AND DEVICE FOR SETTING THE FOCAL SPOT POSITION OF AN X-RAY TUBE BY REGULATION

(75) Inventors: Josef Deuringer, Herzogenaurach (DE); Rolf Gurtner, Erlangen (DE); Karsten Zeiske, Celle (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/757,307

(22) Filed: Jan. 14, 2004

(65) Prior Publication Data

US 2004/0190682 A1 Sep. 30, 2004

(30) Foreign Application Priority Data

Jan. 14, 2003 (DE) ................................ 103 01 071

(51) Int. Cl.
*A61B 6/08* (2006.01)

(52) U.S. Cl. ........................ 378/205; 378/113; 378/137

(58) Field of Classification Search ................ 378/113, 378/137, 205

See application file for complete search history.

(56) References Cited

U.S. PATENT DOCUMENTS 5,550,889 A * 8/1996 Gard et al. ................. 378/113
5,581,591 A * 12/1996 Burke et al. ................ 378/135

* cited by examiner

*Primary Examiner*—Craig E. Church
(74) *Attorney, Agent, or Firm*—Schiff Hardin LLP

(57) ABSTRACT

In a method and a device for setting the focal spot position of an X-ray tube the focal spot position is regulated as a controlled variable by a closed loop regulation circuit. A deflector deflects the electron beam of the X-ray tube depending on a deflection signal, a deflection closed loop regulator generates the deflection signal depending on a focal spot position signal. A measurement arrangement measures a focal spot position signal. The deflector, the deflection closed loop regulator and the measurement arrangement form a closed loop regulation circuit with the focal spot position as the controlled variable and with the deflection signal as the control parameter.

2 Claims, 2 Drawing Sheets

METHOD AND DEVICE FOR SETTING THE FOCAL SPOT POSITION OF AN X-RAY TUBE BY REGULATION

BACKGROUND OF THE INVENTION

1. Field of the Invention

The present invention concerns a device and a process for setting the focal spot position of the electron beam on the anode of an X-ray tube.

2. Description of the Prior Art

X-ray tubes are used in X-ray devices in order to generate X-radiation. Electrons from a cathode are accelerated in the X-ray tube through an electric field at the X-ray voltage to an anode. When they strike the anode, the electrons create characteristic X-radiation as a result of their kinetic energy. The direction and shape of the X-rays that are generated are determined by the quality and orientation of the surface of the anode as well as by the direction and focal spot position of the electron beam when it strikes the anode. In order to create a bundled and intensive X-ray beam in the desired direction, the electron beam is focused and directed at a specific point on the anode surface.

While electric fields are also used to focus the electron beam, its deflection is usually caused by magnetic fields. These are created by deflection coils, which are arranged between the cathode and the anode around the electron beam or the X-ray tube. Depending on the requirements for the sharpness of the focus, the complexity of the focal spot contour, and the options for deflecting the electron beam, one or more deflection coil are provided.

The magnetic field created by the coils varies depending on the coil current. Variations of the coil current thus cause variations in the focal spot position. With application-dependent changes in the X-ray voltage, with which the electrons are accelerated from the cathode to the anode of the X-ray tube, the coil current must also be changed in order to attain the retention of the focal spot position; thus, the coil current vanes depending on the X-ray voltage.

For permanent retention of the desired focal spot position, the coil current of the X-ray voltage must be updated sufficiently quickly. It must also be supplied sufficiently exactly in order to ensure a stable focal spot position. Moreover, fluctuations in the X-ray voltage must be correctable by changing the coil current and an appropriate behavior must be ensured during failures in the X-ray voltage as a result of X-ray arcing.

Regardless of how the electric or magnetic fields for deflection of the electron beam are created, their field strength must take into consideration the currently existing X-ray voltage. The X-ray voltage can either be tapped from the voltage generator, which requires an additional connection between the generator and the deflection device, or it can be tapped from the current X-ray tube voltage. For this, a voltage divider, from which a signal can be tapped proportional to the X-ray voltage, is connected between the high voltage and ground either on the X-ray tube or on the X-ray generator on the anode side as well as on the cathode side.

A control signal, which sets the strength of the electric or magnetic fields for deflecting the electron beam, is generated from this signal from a control electronics assembly in accordance with a stored characteristic curve. If several deflection devices are available in different orientations, then the orientation of the deflection through the characteristic curves is taken into consideration. This concerns control in the classic sense, for which there is no mutual dependency between the focal spot position as the controlled variable and the deflection field as the controlled parameter.

The voltage dividers for tapping the signal proportional to the X-ray voltage represent stray capacitances, which vary over time and are susceptible to disturbances. The electrical connection between the deflection control and the tapping of the high voltage signal also possesses stray capacitances and disturbance inductivities as possible sources of errors. Last but not least, the production tolerances of the X-ray tube, fluctuations in the voltage supply of the X-ray generator, and other unforeseeable disturbances create sources of errors. None these unforeseeable disturbances are taken into consideration in the characteristic curve that is stored for the deflection control and are thus not compensated from the very outset.

SUMMARY OF THE INVENTION

An object of the invention is to provide a device and a method with the focal spot position set in an X-ray tube so that not only the foreseeable but all unforeseeable variations and fluctuations in the inflow sizes that are significant for the focal point position are compensated quickly and reliably.

Another object of the invention is to provide a device and a method for enabling the setting of the focal point position in an X-ray tube without measuring the X-ray voltage.

This object is achieved in accordance with the invention by performing the setting of the focal point position of the X-ray tube through regulation (closed loop control) instead of conventional control. Regulation is meant in the classic sense where the setting of the focal point position as a controlled variable is performed based on a control parameter, whereby the control parameter in turn is set depending on the controlled variable. The control parameter and controlled variable thus affect each other mutually in the regulation.

The regulation of the focal spot position has the advantage that all foreseeable and unforeseeable disturbing influences on the setting of the focal spot position are automatically compensated. Moreover, loss of time, which occurred in conventional devices through the measuring of the X-ray voltage and the subsequent determination of values from a saved characteristic curve, is avoided. Furthermore, through regulation, the measurement of the X-ray voltage and the electrical connection required for this can be foregone, so the associated disturbing influences can be avoided. Last but not least, disturbances as may occur within the regulation circuit are automatically compensated through regulation.

In an embodiment of the invention sensors are provided that measure a signal that reflects the focal spot position. This signal is used as a controlled variable for the deflection regulation, depending on which the strength of the electric field or magnetic field is varied for deflecting the electron beam as the control parameter. Therewith, a signal representing the controlled variable is immediately available to the regulation circuit.

In another embodiment of the invention the controlled variable, i.e., the measured signal for the focal spot position, is measured without touching the X-ray tube or the anode of the X-ray tube. The measurement can take place either on the X-ray itself or optically through temperature measurement on the anode.

The use of complicated connection technologies between the signal detectors of the regulation variable and the X-ray tube thus can be avoided. Moreover, disturbing influences caused by such connections are avoided.

In another embodiment of the invention the intensity of the spatial resolution of the intensity of the X-ray beam is measured as a signal for the focal spot position. This is based on the recognition that the orientation and position of the X-ray depends on the focal spot position. The use of the X-ray intensity as the measured signal has the advantage that the measurement is performed on the actual subject of interest, namely on the X-ray beam itself. Thus, any errors that enter into the generation of the X-ray beam are identified and compensated, regardless of the point in the generation of the X-ray beam where they occur. Moreover, the advantage is attained that the sensors are not complex and are inexpensive and can be easily integrated, since their placement is not critical.

In another embodiment of the invention spatial resolution of the temperature of the anode is measured as the measured signal. Measurement occurs optically, e.g. with infrared cameras and is based on the recognition that the anode is severely heated by the incident electron beam and the highest temperature is found in the focal spot itself. The use of this signal has the advantage that it directly reflects the regulation variable. Disturbing influences as with indirect measurement of the controlled variable from the regulation circuit are thereby eliminated.

DESCRIPTION OF THE PREFERRED EMBODIMENTS

Figure 1:
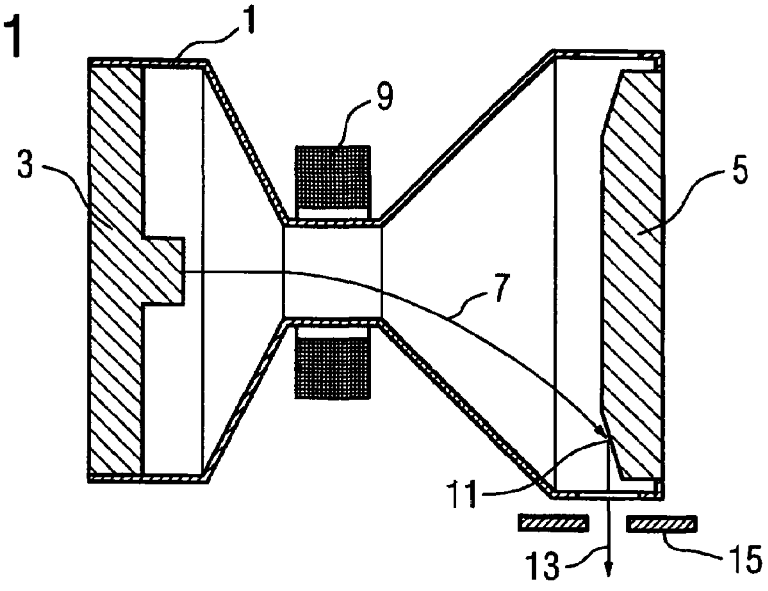
FIG. 1 shows an X-ray tube with the electron beam and X-ray beam in accordance with the invention.

FIG. 1 schematically shows an arrangement for the regulation of the focal spot position of an X-ray tube 1. In the X-ray tube 1, electrons are emitted from the cathode 3 and are accelerated to the anode 5 due to the applied X-ray voltage. The electrons leave the cathode 3 already focused and thus form an electron beam 7. The electron beam 7 is deflected by deflection coils 9 and thus has a curved optical path. Although deflection coils 9 are common for deflecting the electron beam 7, deflection plates or other devices can also be used to create electromagnetic fields.

The electron beam 7 strikes the anode 5 in the focal spot 11. The position of the focal spot 11 depends on the strength of the deflection field created by the deflection coils 9 as well as the kinetic energy of the electrons caused by the X-ray voltage. The width of the electron beam 7 can be influenced by additional measures for focusing. When the anode 5 is struck, the electrons generate characteristic X-radiation. Moreover, the anode 5 is heated in the focal spot.

The generated X-rays are emitted from the anode 5 in an X-ray beam 13. The direction or orientation of the X-ray beam 13 mainly depends on the direction of the electron beam 7, the position of the focal spot 11, as well as the quality and orientation of the surface of the anode 5. The same is true for the spatial position of the X-ray beam 13. A change in the deflection of the electron beam 7 causes a displacement of the focal spot position 11 and thus of the original location of the X-ray beam 13. Moreover, the angle is changed at which the electron beam 7 strikes the surface of the anode 5, which is also why the X-ray beam 13 with a changed angle is emitted from the anode 5.

The X-ray beam 13 exits the X-ray tube 1 and passes through an aperture 15, and traverses an optical path from the anode 5 to the patient or object to be examined or treated.

Figure 2:
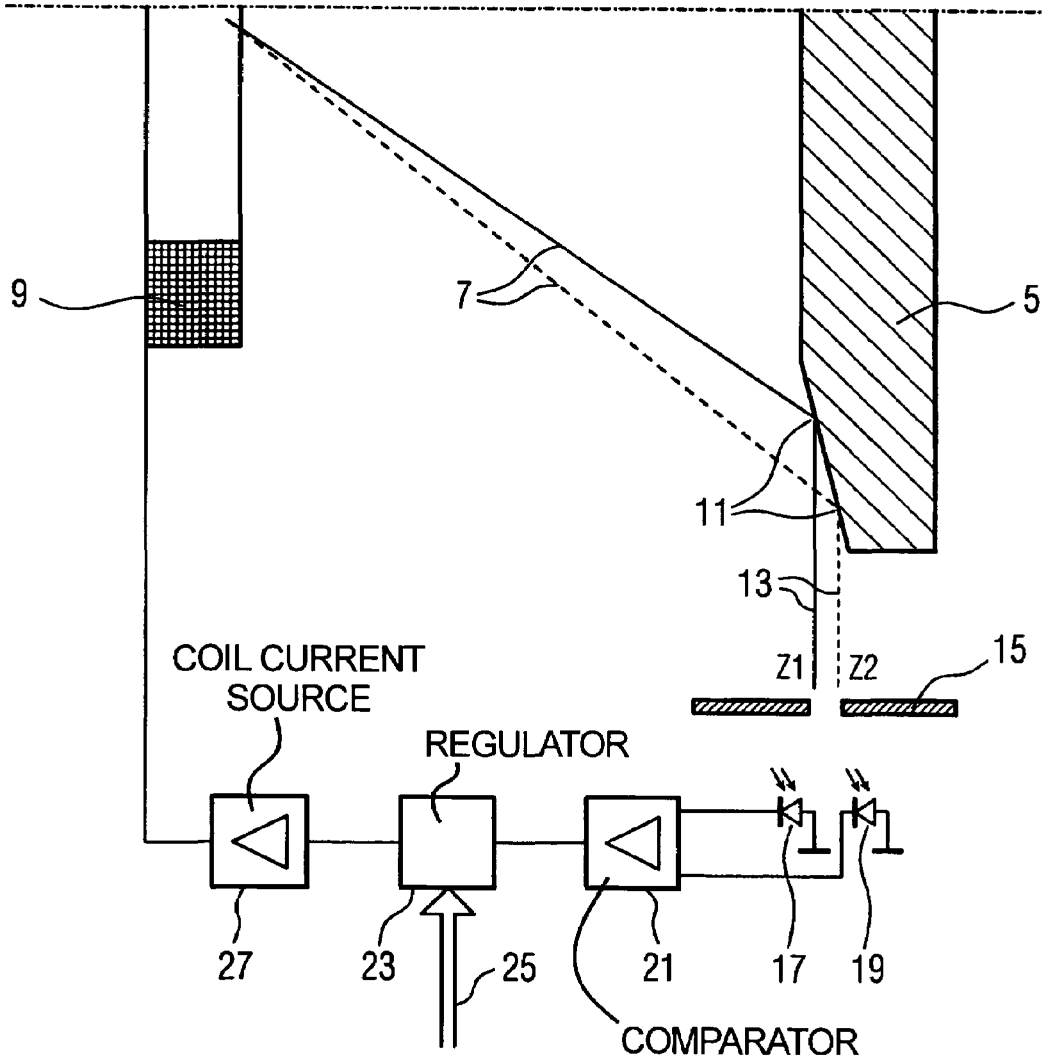
FIG. 2 is a schematic block diagram for regulation of the focal spot position using intensity measurement in accordance with the invention.

FIG. 2 schematically shows a layout for regulation of the focal spot position. Only a section of half of the X-ray tube 1 from FIG. 1 is shown. The electron beam 7 deflected by the deflection coils 9 is depicted in two different, alternative deflection directions, once as a solid line and once as a dashed line. As a result, the electron beam 7 strikes the anode 5 at two different, alternative focal spot positions 11. Depending on focal spot position 11, the anode 5 emits a differently angled X-ray beam 13 with a different spatial position, whereby FIG. 2 only shows the different position and not the different direction. FIG. 2 shows that the different deflection of the electron beam 7 results in a displacement of the position of the X-ray beam 13.

The X-ray beam 13 leaves the X-ray rube 1 and pass through the aperture 15. The aperture 15 traverses the optical path between anode 5 and the object or patient to be examined or treated and shields other emission directions for the X-ray beam 13. It thereby has such a large cross-section that the direction and position of the penetrating X-ray beam 13 can still be modified.

Two photo-detectors 17, 19 for measurement of the position of the X-ray beam 13 are arranged on the other side of the aperture 15, i.e. outside of the X-ray tube 1. Semiconductor detectors, organic photodiodes, or scintillation chambers can be used as photo-detectors 17, 19. The X-ray beam 13 passes through on the optical path provided for it between the two photo-detectors 17 and 19 and thereby hits it at the most on the edge. The usable intensity of the X-ray beam 13 is not decreased by this. The photo-detectors 17, 19 for this constellation provide a low or no output signal. If the X-ray beam 13 is displaced in one or the other direction away from the optical path provided for it, then the output signal of one of the two photo-detectors 17, 19 will be larger and that of the other one will be smaller or remains zero. The output signals of the photo-detectors 17, 19 thus mirror the orientation of the X-ray beam 13 and the focal spot position 11, The photo-detectors 17, 19 are connected with an evaluation component 21, e.g. a differential amplifier. The output signal of the comparator 21 reflects the relationship of the output signal of the photo-detectors 17, 19 to each other and thus the orientation of the X-ray beam 13. Depending on the layout of the arrangement, a negative output signal can, for example, indicate a displacement of the X-ray beam 13 to the left, a positive output signal can indicate a displacement to the right, and a substantially zero output signal can indicate the exact centering of the X-ray beam 13.

The output signal of the comparator 21 is fed to a regulator 23. The regulator 23 receives, via another input, the target value input 25, a target value signal, which reflects the desired position of the X-ray beam 13 in relation to the photo-detectors 17, 19. Depending on the adherence or the deviation of the output signal of the comparator 21 from the target value, the regulator 23 gives a consistent or changed output signal. This is amplified by a coil current source 27 and is supplied to the deflection coil 9 as coil current.

The depicted layout operates as a regulation circuit in that the regulator 23 changes the coil current as the regulation parameter, which results in a changed deflection of the electron beam 7. This changes the regulation variable, namely the focal spot position 11 of the electron beam 7 on the anode 5. The regulation variable cannot be obtained directly, but rather only indirectly via the position of the X-ray beam 13 through the photo-detectors 17, 19. This indirectly obtained regulation control variable is fed to the regulator 23. With this, the regulation circuit is closed, since the indirectly attained regulation variable also reliably reflects the actual focal spot position 11. The time constant, with which the regulation circuit works, is determined only from the time constants and response times of the components of the regulation circuit itself. Above all, the aperture time through the photo-detectors 17, 19 should be taken into account and should be as short as possible. The comparator 21 operates virtually without a time delay; the regulator 23 and the coil current source 27 should operate sufficiently quickly so as to be compatible.

The regulation circuit offers the advantages typical for a regulation circuit, which include disturbing influences being automatically compensated within the regulation circuit. For example, unintended fluctuations of the regulation parameter, the coil current, lead to a change in the regulation variable, namely the focal spot position 11, however as such they are detected and thus re-compensated through the photo-detectors 17, 19. Fluctuations in the X-ray voltage also lead to a changed focal spot position 11 and are also detected by the photo-detectors 17, 19 and compensated by the regulation circuit. This also applies to other foreseeable and unforeseeable disturbing influences.

Figure 3:
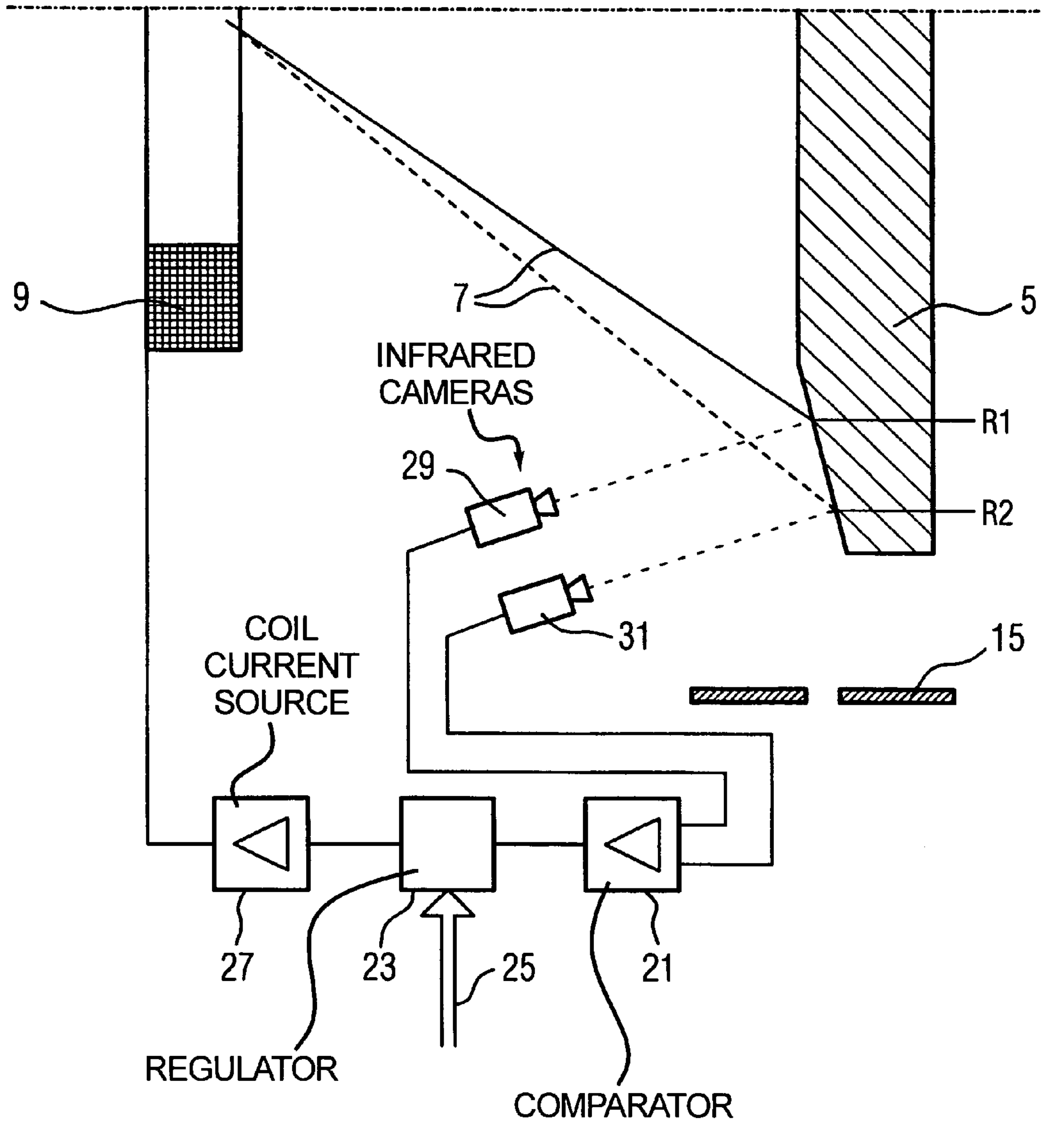
FIG. 3 is a schematic block diagram for regulation of the focal spot position using optical temperature measurement in accordance with the invention.

FIG. 3 schematically shows a different version of the layout for regulation of the focal spot position. FIG. 3 shows the same section as in FIG. 2 with mainly the same components, However, instead of the photo-detectors 17, 19, infrared cameras 29, 31 are provided. The infrared cameras 29, 31 are arranged in such a manner that they measure the temperature of the anode 5 at different positions R1, R2. This measurement takes place outside of the X-ray tube 1, which is made for this purpose of an infrared-permeable material or has an infrared-permeable window.

The electrons striking the anode 5 cause a severe heating of the anode 5 due to their kinetic energy. The heat is also distributed, but reaches its peak value in the focal spot 11. Thus, depending on the orientation of the electron beam 7 or focal spot position 11, different temperatures are to be measured in the different measurement points R1, R2. The positions R1, R2 on the surface of the anode 5, measured by the infrared cameras 29, 31, are positioned so that the electron beam 7 strikes between them with the correct deflection. Changes in the focal spot position 11 will then be discernable as changes in the measurement signals in R1, R2. The temperature measurement signals only form the focal spot position indirectly, but sufficiently reliably to be able to serve as a signal for the control variable. The regulation circuit thus functions based on temperature measurement as well as based on X-ray intensity measurement. The description of the function of the regulation circuit is thus analogous to the description for FIG. 2 and therefore need not be repeated.

The described single-channel regulation circuit can be expanded to a multiple-channel regulation circuit for the two-dimensional regulation of the focal spot position using additional deflection coils 9 as well as additional detectors 17, 19, 29, 31.

Accordingly, the regulator 23 can have several inputs for signals from comparators 21 and target values 25.

At the beginning of operation, the regulator 23 sets a predetermined start value for the regulation parameter. This ensures that, at the beginning of operation, the electron beam 7 hits an area on the anode 5 that enables for the very beginning recording by the detectors 17, 19, 29, 31. Otherwise the regulation circuit would not be able to function due to the absence of the regulation variable. The start value can be determined depending on the target value of the X-ray voltage, but without the X-ray. voltage needing to be measured. The avoidance of a measurement of the X-ray voltage prevents paths of disturbance from the X-ray tube 1 to the regulation circuit as well as disturbances through stray capacitances and residual inductivities in the connection of the two.

The start value for the regulator 23 can also be set when short circuits occur in the X-ray tube 1 and thus when the electron beam 7 and the X-ray beam 13 fail. After operation is restarted subsequent to a short circuit, this also ensures that the regulation circuit can be active.

Although modifications and changes may be suggested by those skilled in the art, it is the intention of the inventors to embody within the patent warranted hereon all changes and modifications as reasonably and properly come within the scope of their contribution to the art.

What is claimed is:

1. An x-ray device comprising:

an x-ray tube comprising a cathode that emits an electron beam, and an anode that is struck by said electron beam at a focal spot at a focal position to cause x-rays to be emitted from said focal spot;

a deflector that generates a deflection field that interacts with said electron beam in a propagation path between said cathode and said anode to deflect said electron beam to alter said focal spot position;

a temperature measuring arrangement to measure a temperature of said anode and to generate a focal spot position signal dependent on measurement of said temperature of said anode; and a closed loop regulator connected to said deflector and to said temperature measuring arrangement for regulating said focal spot position in real time during emission of said electron beam, using said deflection field as a controlled variable, dependent on said focal spot position signal as a control variable wherein said measurement arrangement comprises an infrared camera for measuring temperature.

2. A method for operating an x-ray device comprising the steps of:

in an x-ray tube, emitting an electron beam from a cathode onto an anode, said electron beam striking said anode at a focal spot at a focal position, and thereby emitting x-rays from said focal spot;

with an electromagnetic deflector, generating a deflection field to deflect said electron beam in a propagation path between said anode and said anode to alter said focal spot position;

measuring a temperature of said anode with an infrared camera and generating a focal spot position signal, indicative of said focal spot position, from the measured temperature; and regulating generation of said deflection field by said deflector in a closed loop in real time during emission of said electron beam dependent on said focal spot position as a control variable, with said deflection field as a controlled variable.

* * * * *